United States Patent [19]

Sorokin

[11] Patent Number: 5,773,387
[45] Date of Patent: Jun. 30, 1998

[54] HERBICIDAL COMPOSITION COMPRISING TWO 1,3,5-TRIAZINE SULFONYLUREA DERIVATIVES

[75] Inventor: Vladimir Iosifovich Sorokin, Moscow, Russian Federation

[73] Assignee: Labatt Brewing Company Limited, London, Canada

[21] Appl. No.: 392,868

[22] PCT Filed: Sep. 2, 1993

[86] PCT No.: PCT/RU93/00210

§ 371 Date: Nov. 15, 1995

§ 102(e) Date: Nov. 15, 1995

[87] PCT Pub. No.: WO94/05154

PCT Pub. Date: Mar. 17, 1994

[30] Foreign Application Priority Data

Sep. 4, 1992 [RU] Russian Federation ............... 5061714

[51] Int. Cl.$^6$ .............................. A01N 43/68; A01N 43/70
[52] U.S. Cl. ............................................................. 504/134
[58] Field of Search ............................................ 504/134

[56] References Cited

U.S. PATENT DOCUMENTS

| | | | |
|---|---|---|---|
| 3,013,054 | 12/1961 | Richter | 260/473 |
| 5,223,016 | 6/1993 | Takematsu et al. | 504/130 |

FOREIGN PATENT DOCUMENTS

| | | |
|---|---|---|
| 0 108 237 | 5/1984 | European Pat. Off. . |
| 236 273 | 9/1987 | European Pat. Off. . |
| 0 448 723 | 10/1991 | European Pat. Off. . |
| 0 480 306 | 4/1992 | European Pat. Off. . |
| 2 440 158 | 5/1980 | France . |
| 2 609 370 | 7/1988 | France . |
| 5 668 530 | 1/1989 | Switzerland . |

OTHER PUBLICATIONS

Makeeva–guryanova et al., *Sulfonilmochevinynovye perspektivnye gerbitsidy*, obsornaya informatsia, 1989, gosagroprom SSR (Moscow) pp. 20–21, 48–55.

Mel'nikov et al., Khimicheskie sredstva zashchity rasterii', 1980, *Khimiya*, Moscow, p. 27.

Smith, Sulfonylurea herbicides, PJB Publications Ltd., pp. 51, 67, 99, and 107 (1991).

*Primary Examiner*—S. Mark Clardy
*Attorney, Agent, or Firm*—Cammarata & Grandinetti

[57] ABSTRACT

This invention relates to herbicidal compositions containing sulfonylureas useful for control of undesired vegetation by treatment of vegetation or the locus to be protected. To eliminate detrimental effects of herbicides in crop rotation and phytotoxicity to crops by lowering dosage and widening of activity spectrum a novel herbicidal composition is disclosed consisting of diethylethanolammonium salts of 1-(2-chlorobenzenesulfonyl)-3-(4-isopropylydeniminoxy-6-dimethylamino-1,3,5-triazin-2-yl)urea and 1-(2-substituted-benzenesulfonyl)-3-(4-methoxy-6-methyl-1,3,5-triazin-2-yl)urea (e.g. chlorsulfuron and triasulfuron derivatives), a surfactant, an organic solvent and water.

18 Claims, No Drawings

HERBICIDAL COMPOSITION COMPRISING TWO 1,3,5-TRIAZINE SULFONYLUREA DERIVATIVES

This application has been filed under 35 USC 371 as the national stage application of PCT/RU93/00210, filed Sep. 2, 1993.

FIELD OF UTILITY

The instant application is related to agriculture, specifically to chemical agents for plant protection and eradication of undesired vegetation.

BACKGROUND OF THE INVENTION

Derivatives of sulfonylurea are known to possess herbicidal activity.

Specific action of all preparations of sulfonylurea series is related to inhibition of the early stage in amino acid biosynthesis by suppression of enzyme acetolactate synthetase (ALS) activity. A relationship between the herbicidal activity of sulfonylurea derivatives and their ability to inhibit ALS has been established.

The ALS in most of the higher plants is highly sensitive to herbicides of the sulfonylurea series. Nevertheless, the endurance of some plants to said compounds, pointing to unspecific sensitivity to ALS, is connected to inactivation or detoxication of the sulfonylurea derivative. These processes proceed at with different rates in various plants and that results both in high selectivity of herbicidal compositions towards various agricultural species and in resistance developed in weeds. The sulfonylurea derivatives of the instant invention are for use in cereals—e.g., corn, barley, rye and oats.

Most of the known derivatives of the sulfonylurea series are slowly decomposed in soil and overdosage of said herbicides results in detrimental effects in crop rotation as well as to serious phytotoxicity in certain agricultural species, e.g., corn, soybean etc.

All known herbicidal compositions based on sulfonylurea are wettable powders or microgranules. The absence of water-soluble preparations in this series is explainable by low water-solubility of sulfonylureas and their relatively high hydrolysis rate (C. Smith, Sulfonylurea herbicides, 1991, PJB Publication Ltd., pp. 51, 67, 99, and 107).

To counteract said shortcomings a herbicidal composition had to be developed with lower application dosage, wider activity spectrum on weeds and absence of phytotoxicity towards cultivated species.

A herbicidal composition with wide spectrum of activity has been disclosed (EP application #236273) consisting of two sulfonylureas A and B:

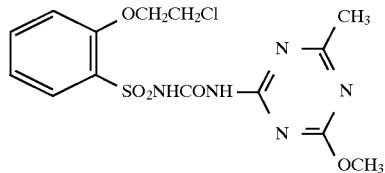

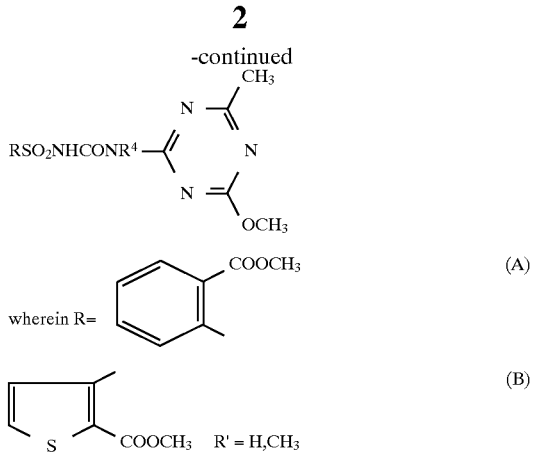

with the addition of a surfactant, an organic solvent and water.

A method for the control of undesired vegetation using said herbicidal composition involves treating the vegetation or soil with said herbicidal composition in the form of an emulsion or suspension in dosage up to 3 kg/ha. The disclosed herbicidal composition displays undesirable phytotoxic effects on such crops as corn, soybean etc.

DETAILED DESCRIPTION OF THE INVENTION

The instant invention discloses a herbicidal composition, comprising a mixture of benzenesulfonylurea derivative (I) in the form of its ammonium salt

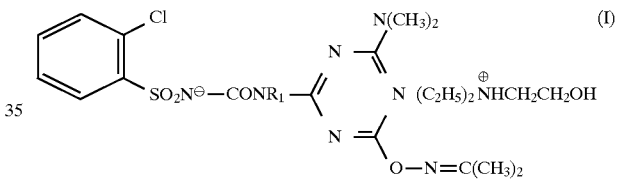

with a benzenesulfonylurea derivative (II) In the form of its ammonium salt

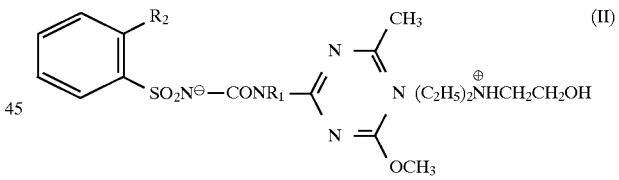

wherein $R_1$ is hydrogen or methyl and $R_2$ is chloro, methoxycarbonyl or 2-chloroethoxy; a surfactant, an organic solvent—triethyleneglycol and water In the following mass percentage:

| | |
|---|---|
| compound of the formula (I) | 1,5–30% |
| compound of the formula (II) | 1,5–30% |
| surfactant | 1,0–5,0% |
| triethyleneglycol | 20–40% |
| water | up to 100% |

As a surfactant an agent selected from the following group is applicable: bis-polyoxyethylated alkylamine, sodium bis(2-ethylhexyl)succinate sulfonate, polyethyleneglycol monoalkyl ethers or alkylaryl ethers of polyethyleneglycol or polypropyleneglycol.

Compound I and its use are described in the following two publications, which are incorporated herein by reference in their entirety:

(1) Author's Certificate No. SU 1782974 (Inventor: Mr. V. Sorokin), published in the Official Russian Gazette ("Izobretenija i . . . ") on Dec. 23, 1992, No. 47/1992; and (2) N. N. Melnikov, *Pesticides and Growth Regulators*, Moscow, *Khimija*, 576 pages, published in 1995, wherein the compound and its preparation are described on pages 504–505 under the title "Chlorsulfoxim" (Krug).

The combination of the two sulfonylureas (I) and (II) in the form of their ammonium salts results in unexpected synergism as evidenced by the results of biological testing.

Herbicidal compositions containing a single sulfonylurea (I) or (II) in the form of its ammonium-salt display a different spectrum of effects on plants. The composition based on sulfonylurea (I) mainly stimulates the growth of crops (wheat, corn, soybean, cotton) and suppresses the growth of weeds (cocklebur, lambsquarters, wild mustard) while the composition based on sulfonylurea (II) is strongly herbicidal to all species except wheat.

The synergism of the mixture consisting of ammonium salts of sulfonylureas (I) and (II) can result both in an increase of the herbicidal action—(+)-synergism and in a decrease of the herbicidal action—(−)-synergism, i.e., antagonism. In the cases where (I) displays the stimulating effect on the growth of plants, e.g., corn, soybean, cotton, the addition of (II) (displaying a pronounced phytotoxicity itself) within limits of (I)>(II), results in (−)-synergism (antagonism). The addition of (I) to (II), i.e., when (I)<(II), results in (+)-synergism.

The quantitative effect of synergism can be calculated by the equation:

$$E = E_o - E_c$$

wherein $E_o$—observed % of plants destroyed by the mixture of compounds;

$E_c$—% of destroyed plants calculated according to Colby:

$$E_c = X + Y - (X+Y)/100$$

wherein

X—the % of destroyed by (I).

Y—the % of plants destroyed by (II).

For example:

on corn, (I)/(IIA)=2/1, E=−58%; (I)/(IIA)=1/2, E=+12%; on cocklebur, (I)/(IIA)=13/1, E=+46%; (I)/(IIA)=1/13, E=+22%.

An analogical effect is displayed in all tests. Thus, application of ammonium salts of the sulfonylureas (I) and (II) makes possible effective control of undesired vegetation while substantially lowering the dosage of each component and reliably protecting such crops as wheat, corn, soybean etc.

The invention is further illustrated by the following examples.

EXAMPLE 1

Diethylethanolammonium Salt of 1-(2-chlorobenzenesulfonyl)-3-(4-isopropylydeniminoxy-6-dimethylamino-1,3,5-triazin-2-yl)urea The reaction vessel was charged with 427 g (1 Mole) of 1-(2-chlorobenzene sulfonyl)-3-(4-isopropylydeniminoxy-6-dimethylamino-1,3,5-triazin-2-yl)urea (I), 117 g (1 Mole) of diethylaminoethanol and 10 L of water and the suspension stirred until solution was complete. The solvent was evaporated on rotary vacuum evaporator and the diethylethanolammonium salt of the sulfonylurea (I) collected in quantitative yield.

By the method described in Example 1 the diethylethanolammonium salts of the benzenesulfonylurea (II) were also prepared. Elemental analyses and physico-chemical data for the diethylethanolammonium salts of the sulfonylureas (I) and (II) are presented in Table 1.

EXAMPLE 2

Herbicidal Composition

The reaction vessel was charged with calculated amounts of the diethylethanolammonium salts of sulfonylureas (I) and (II), calculated amounts of water, triethyleneglycol and surfactant. The mixture was stirred at 20° C. for one hour.

Examples of herbicidal compositions with different quantities of constituents are presented in Table 2.

EXAMPLE 3

Test of Herbicidal Action

Test of herbicidal composition 1.1 (Example 1 from Table 1) was carried out under laboratory conditions applying 100 g/ha of the composition with concentration of ammonium salts of sulfonylureas ranging from 1.5 to 30% of the mass of composition.

As the test crops and weeds the following plants were used:

monocotyledonous—wheat, corn;

dicotyledonous—lambsquarters, soybean, flax, cotton, cocklebur wild mustard.

Treatment of the vegetation was carried out:

for cereals—at the third leaf phase;

for soybean—at the tripple leaf phase;

for other species—at the second true leaf phase.

Soil humidity was kept at 60–70% of saturation by daily watering.

The effectivity of the herbicidal compositions was established by comparing plants treated with test compositions and with etalon herbicides and controls on 14th day after treatment.

The results of testing are summarized in Tables 3–6.

The disclosed combination of the sulfonylurea derivative (I) and derivatives of substituted benzenesulfonamide (II) results in an unexpected synergism as evidenced by the results of biological testing. Herbicides containing an ammonium salt of sulfonylurea (I) or an ammonium salt of substituted benzenesulfonamide derivatives (II) display different effects on plants. Thus, sulfonylurea (I) (the top row of data in each of Tables 3–6) mainly stimulates the growth of crops (wheat, corn, soybeans, cotton), but suppresses the growth of weeds (cocklebur, lambsquarters, wild mustard). The derivatives of substituted benzenesulfonamide (II) (the far left column data in each of Tables 3–6) are strongly herbicidal to all plant species except wheat.

The data in Tables 3–6 show that for crops there is a wide range of concentrations of herbicidal compositions that either stimulate the growth of crops or do not significantly influence their growth. In the same ranges there are specific compositions that selectively inhibit the growth of certain weeds. These data show that there is not a linear additivity of the effects of the components of the composition, but that new and unexpected biological effects take place, thus making the disclosed compositions advantageous as compared with the single components.

An analogical effect is displayed in all tests. Thus, the application of herbicidal compositions on the basis of mixtures containing ammonium salts of sulfonylurea (I) and derivatives of substituted benzenesulfonamides (II) makes possible the effective control of undesired vegetation while substantially lowering the dosage of each component and reliable protection of the such crops as wheat, corn, soybeans, and the like.

TABLE 1

Elemental analyses and physico-chemical data of diethylethanolammonium salts of (I) and (II)

| Structural formula | Summary formula | Elemental analysis calcul. | | found | M.p. °C. | $cm^{-1}$ | nm |
|---|---|---|---|---|---|---|---|
| (I) 2-Cl-C6H4-SO2N(−)CONH-[triazine with N=C(CH3)2-O− and N(CH3)2]; (C2H5)2NH(+)CH2CH2OH | $C_{21}H_{33}ClN_8O_5S$ | C 46.3<br>H 6.1<br>N 20.6 | | 46.5 46.4<br>6.1 6.0<br>20.7 20.6 | 125–7 | 1650 | 240 |
| (IIA) 2-Cl-C6H4-SO2N(−)CONH-[triazine with CH3 and OCH3]; (C2H5)2NH(+)CH2CH2OH | $C_{18}H_{27}ClN_6O_3S$ | C 45.6<br>H 5.7<br>N 17.7 | | 45.7 45.6<br>5.5 5.6<br>17.9 18.0 | 142–6 | 1651 | 234 |
| (IIB) 2-CO2CH3-C6H4-SO2N(−)CONH-[triazine with CH3 and OCH3]; (C2H5)2NH(+)CH2CH2OH | $C_{20}H_{30}N_6O_7S$ | C 48.2<br>H 6.0<br>N 16.2 | | 48.3 48.4<br>6.1 5.9<br>16.7 16.6 | 123–5 | 1642 | 238 |
| (IIC) 2-OCH2CH2Cl-C6H4-SO2N(−)CONH-[triazine with CH3 and OCH3]; (C2H5)2NH(+)CH2CH2OH | $C_{20}H_{31}ClN_6O_6S$ | C 46.3<br>H 6.0<br>N 16.2 | | 46.5 46.4<br>6.0 5.9<br>16.0 16.3 | 154–8 | 1655 | 238 |
| (IID) 2-CO2CH3-C6H4-SO2N(−)CON(CH3)-[triazine with CH3 and OCH3]; (C2H5)2NH(+)CH2CH2OH | $C_{21}H_{32}N_6O_7S$ | C 49.2<br>H 6.3<br>N 16.4 | | 49.1 49.3<br>6.2 6.1<br>16.4 16.2 | 120–7 | 1645 | 241 |

TABLE 2

| Herbicidal composition | Percentage of components | | | | |
|---|---|---|---|---|---|
| 1.1 Diethylethanolammonium salt of (I) | 1.5 | 1.5 | 10 | 30 | 30 |
| Diethylethanolammonium salt of (II) (IIA, IIB, IIC, IID) | 1.5 | 30 | 10 | 1.5 | 30 |
| Surfactant | 1 | 2.5 | 2 | 2.5 | 5 |
| Triethyleneglycol | 40 | 30 | 35 | 30 | 20 |
| Water | 56 | 365 | 43 | 36 | 15 |

TABLE 3

Herbicidal activity of composition 1.1 {compound(I) + compound(IIA)}

Wheat

| IIA\I | 0 | 1,5 | 5 | 10 | 20 | 30 |
|---|---|---|---|---|---|---|
| 0 |  | +5 | +15 | +18 | +8 | +12 |
| 1,5 | +2 | +5 | +6 | +32 | +6 | +8 |
| 5 | +6 | +3 | +8 | +7 | 0 | +13 |
| 10 | 0 | 0 | +4 | 0 | +3 | +9 |
| 20 | 13 | 14 | 3 | 6 | 2 | +14 |
| 30 | 21 | 27 | 14 | 12 | 7 | 0 |

Lambsquarters

| IIA\I | 0 | 1,5 | 5 | 10 | 20 | 30 |
|---|---|---|---|---|---|---|
| 0 |  | 18 | 25 | 48 | 70 | 81 |
| 1,5 | 46 | 72 | 71 | 72 | 78 | 88 |
| 5 | 85 | 88 | 88 | 82 | 83 | 100 |
| 10 | 100 | 100 | 100 | 100 | 94 | 96 |
| 20 | 100 | 100 | 100 | 100 | 100 | 100 |
| 30 | 100 | 100 | 100 | 100 | 100 | 100 |

Corn

| IIA\I | 0 | 1,5 | 5 | 10 | 20 | 30 |
|---|---|---|---|---|---|---|
| 0 |  | +4 | +8 | +15 | +12 | 2 |
| 1,5 | 27 | +2 | +4 | +6 | +4 | 0 |
| 5 | 35 | 42 | 0 | +9 | +4 | +8 |
| 10 | 48 | 54 | 51 | 5 | +16 | 8 |
| 20 | 72 | 83 | 79 | 68 | 51 | 42 |
| 30 | 81 | 91 | 93 | 96 | 79 | 63 |

Cotton

| IIA\I | 0 | 1,5 | 5 | 10 | 20 | 30 |
|---|---|---|---|---|---|---|
| 0 |  | +8 | +12 | +23 | +11 | 8 |
| 1,5 | 12 | +6 | +5 | +2 | +18 | +12 |
| 5 | 23 | 0 | +2 | +4 | +2 | +13 |
| 10 | 41 | 23 | 38 | 0 | +12 | +8 |
| 20 | 67 | 58 | 66 | 42 | 21 | +4 |
| 30 | 72 | 86 | 88 | 81 | 64 | 34 |

Soybean

| IIA\I | 0 | 1,5 | 5 | 10 | 20 | 30 |
|---|---|---|---|---|---|---|
| 0 |  | +8 | +12 | +17 | +9 | +12 |
| 1,5 | 28 | 15 | 7 | +15 | +33 | +13 |
| 5 | 47 | 58 | 47 | +16 | +13 | 18 |
| 10 | 87 | 81 | 89 | 58 | +13 | 9 |
| 20 | 97 | 98 | 100 | 100 | 66 | 13 |
| 30 | 100 | 100 | 100 | 100 | 100 | 77 |

Flax

| IIA\I | 0 | 1,5 | 5 | 10 | 20 | 30 |
|---|---|---|---|---|---|---|
| 0 |  | 0 | +2 | +8 | +3 | 5 |
| 1,5 | 11 | 17 | 12 | 9 | 8 | 0 |
| 5 | 20 | 16 | 12 | 9 | 5 | 2 |
| 10 | 26 | 23 | 18 | 14 | 9 | 4 |
| 20 | 20 | 21 | 20 | 18 | 16 | 11 |
| 30 | 28 | 29 | 26 | 18 | 19 | 13 |

Cocklebur

| IIA\I | 0 | 1,5 | 5 | 10 | 20 | 30 |
|---|---|---|---|---|---|---|
| 0 |  | 0 | 0 | 12 | 12 | 17 |
| 1,5 | 10 | 57 | 54 | 70 | 70 | 79 |
| 5 | 17 | 66 | 76 | 73 | 73 | 81 |
| 10 | 61 | 72 | 84 | 64 | 64 | 73 |
| 20 | 71 | 86 | 93 | 78 | 78 | 86 |
| 30 | 77 | 91 | 97 | 100 | 100 | 91 |

Wild mustard

| IIA\I | 0 | 1,5 | 5 | 10 | 20 | 30 |
|---|---|---|---|---|---|---|
| 0 |  | 13 | 31 | 43 | 58 | 65 |
| 1,5 | 58 | 49 | 48 | 72 | 82 | 83 |
| 5 | 76 | 58 | 61 | 69 | 83 | 86 |
| 10 | 89 | 81 | 74 | 89 | 81 | 92 |
| 20 | 100 | 93 | 90 | 94 | 100 | 87 |
| 30 | 100 | 100 | 98 | 99 | 100 | 100 |

TABLE 4

Herbicidal activity of composition 1.1 {compound(I) + compound(IIB)}

Wheat

| IIB\I | 0 | 1,5 | 5 | 10 | 20 | 30 |
|---|---|---|---|---|---|---|
| 0 |  | +5 | +15 | +18 | +8 | +12 |
| 1,5 | 0 | 0 | +2 | +8 | +8 | +8 |
| 5 | 0 | 4 | 8 | +4 | +4 | 6 |
| 10 | 8 | 11 | 13 | 8 | 4 | 4 |
| 20 | 16 | 21 | 19 | 17 | 17 | 10 |
| 30 | 24 | 29 | 30 | 21 | 22 | 18 |

Lambsquarters

| IIB\I | 0 | 1,5 | 5 | 10 | 20 | 30 |
|---|---|---|---|---|---|---|
| 0 |  | 18 | 25 | 48 | 70 | 81 |
| 1,5 | 63 | 82 | 84 | 80 | 79 | 91 |
| 5 | 88 | 93 | 92 | 91 | 92 | 89 |
| 10 | 100 | 100 | 96 | 91 | 9 | 88 |
| 20 | 100 | 100 | 100 | 98 | 100 | 96 |
| 30 | 100 | 100 | 100 | 100 | 100 | 100 |

Corn

| IIB\I | 0 | 1,5 | 5 | 10 | 20 | 30 |
|---|---|---|---|---|---|---|
| 0 |  | +4 | +8 | +15 | +2 | 2 |
| 1,5 | 21 | +6 | +7 | +11 | 5 | 11 |
| 5 | 27 | +33 | 6 | +3 | 1 | 14 |
| 10 | 52 | 64 | 65 | 7 | +2 | 9 |
| 20 | 68 | 69 | 73 | 68 | 19 | 6 |
| 30 | 74 | 83 | 79 | 81 | 79 | 25 |

Cotton

| IIB\I | 0 | 1,5 | 5 | 10 | 20 | 30 |
|---|---|---|---|---|---|---|
| 0 |  | +8 | +12 | +23 | +11 | 8 |
| 1,5 | 9 | +1 | +14 | +27 | +37 | +14 |
| 5 | 16 | 13 | +8 | +7 | +6 | +17 |
| 10 | 57 | 32 | 22 | +4 | +16 | +11 |
| 20 | 69 | 48 | 53 | 42 | 4 | +30 |
| 30 | 81 | 63 | 59 | 67 | 72 | 19 |

Soybean

| IIB\I | 0 | 1,5 | 5 | 10 | 20 | 30 |
|---|---|---|---|---|---|---|
| 0 |  | +8 | +12 | +17 | +9 | +12 |
| 1,5 | 21 | 6 | +7 | +11 | 5 | +15 |
| 5 | 38 | 39 | 21 | +3 | 1 | 14 |
| 10 | 48 | 49 | 59 | 40 | +2 | 9 |
| 20 | 81 | 76 | 69 | 72 | 78 | 6 |
| 30 | 100 | 100 | 100 | 100 | 100 | 77 |

Flax

| IIB\I | 0 | 1,5 | 5 | 10 | 20 | 30 |
|---|---|---|---|---|---|---|
| 0 |  | 0 | +2 | +8 | +3 | 5 |
| 1,5 | 13 | 16 | 13 | 10 | +11 | 0 |
| 5 | 14 | 13 | 22 | 7 | 12 | +2 |
| 10 | 23 | 22 | 20 | 17 | 17 | 6 |
| 20 | 33 | 21 | 24 | 15 | 28 | 27 |
| 30 | 28 | 29 | 26 | 18 | 27 | 34 |

Cocklebur

| IIB\I | 0 | 1,5 | 5 | 10 | 20 | 30 |
|---|---|---|---|---|---|---|
| 0 |  | 0 | 0 | +2 | 12 | 17 |
| 1,5 | 33 | 74 | 52 | 72 | 66 | 74 |
| 5 | 42 | 58 | 79 | 70 | 78 | 80 |

Wild mustard

| IIB\I | 0 | 1,5 | 5 | 10 | 20 | 30 |
|---|---|---|---|---|---|---|
| 0 |  | 13 | 31 | 43 | 58 | 65 |
| 1,5 | 61 | 73 | 77 | 86 | 82 | 74 |
| 5 | 83 | 87 | 86 | 89 | 96 | 89 |

TABLE 4-continued

Herbicidal activity of composition 1.1 {compound(I) + compound(IIB)}

| 10 | 68 | 74 | 81 | 86 | 78 | 86 | 10 | 100 | 94 | 96 | 100 | 92 | 96 |
| 20 | 83 | 88 | 91 | 93 | 95 | 87 | 20 | 100 | 100 | 100 | 100 | 100 | 100 |
| 30 | 100 | 100 | 100 | 100 | 100 | 96 | 30 | 100 | 100 | 100 | 100 | 100 | 100 |

TABLE 5

Herbicidal activity of composition 1.1 {compound(I) + compound(IIC)}

| Wheat | | | | | | | Lambsquarters | | | | | | |
|---|---|---|---|---|---|---|---|---|---|---|---|---|---|
| IIC\I | 0 | 1,5 | 5 | 10 | 20 | 30 | IIC\I | 0 | 1,5 | 5 | 10 | 20 | 30 |
| 0 |  | +5 | +15 | +18 | +8 | +12 | 0 |  | 18 | 25 | 48 | 70 | 81 |
| 1,5 | 0 | +2 | 0 | +17 | +18 | 0 | 1,5 | 71 | 97 | 92 | 79 | 82 | 77 |
| 5 | 0 | 0 | 2 | +4 | +4 | 6 | 5 | 92 | 100 | 100 | 91 | 82 | 79 |
| 10 | 0 | 0 | 0 | +4 | +4 | 7 | 10 | 95 | 100 | 100 | 100 | 96 | 86 |
| 20 | 8 | 0 | 4 | 0 | 0 | +2 | 20 | 100 | 100 | 100 | 100 | 100 | 100 |
| 30 | 6 | 5 | 2 | 3 | 7 | 17 | 30 | 100 | 100 | 100 | 100 | 100 | 100 |
| Corn | | | | | | | Cotton | | | | | | |
| IIC\I | 0 | 1,5 | 5 | 10 | 20 | 30 | IIC\I | 0 | 1,5 | 5 | 10 | 20 | 30 |
| 0 |  | +4 | +8 | +15 | +12 | 2 | 0 |  | +8 | +12 | +23 | +11 | 8 |
| 1,5 | 48 | 12 | +6 | +8 | +13 | 8 | 1,5 | 0 | 7 | 6 | +5 | +13 | +5 |
| 5 | 64 | 38 | 17 | 0 | +14 | 14 | 5 | 8 | 10 | 8 | 4 | 0 | +4 |
| 10 | 72 | 48 | 38 | 31 | +13 | 0 | 10 | 14 | 8 | 10 | 12 | 12 | 12 |
| 20 | 86 | 63 | 59 | 42 | 28 | 27 | 20 | 48 | 32 | 26 | 20 | 18 | 8 |
| 30 | 88 | 72 | 69 | 55 | 48 | 46 | 30 | 62 | 54 | 48 | 29 | 42 | 37 |
| Soybean | | | | | | | Flax | | | | | | |
| IIC\I | 0 | 1,5 | 5 | 10 | 20 | 30 | IIC\I | 0 | 1,5 | 5 | 10 | 20 | 30 |
| 0 |  | +8 | +12 | +17 | +9 | +12 | 0 |  | 0 | +2 | +8 | +3 | 5 |
| 1,5 | 33 | 27 | 12 | +17 | +11 | +6 | 1,5 | 16 | 16 | 12 | 8 | 4 | 7 |
| 5 | 41 | 38 | 22 | 17 | +12 | 6 | 5 | 24 | 19 | 24 | 11 | 8 | 6 |
| 10 | 62 | 39 | 47 | 48 | 24 | +3 | 10 | 18 | 16 | 19 | 17 | 8 | 9 |
| 20 | 87 | 64 | 58 | 55 | 57 | 17 | 20 | 31 | 27 | 22 | 21 | 19 | 8 |
| 30 | 74 | 82 | 76 | 78 | 66 | 62 | 30 | 33 | 23 | 26 | 18 | 21 | 26 |
| Cocklebur | | | | | | | Wild mustard | | | | | | |
| IIC\I | 0 | 1,5 | 5 | 10 | 20 | 30 | IIC\I | 0 | 1,5 | 5 | 10 | 20 | 30 |
| 0 |  | 0 | 0 | +2 | 12 | 17 | 0 |  | 24 | 33 | 43 | 58 | 65 |
| 1,5 | 33 | 46 | 42 | 58 | 55 | 62 | 1,5 | 61 | 68 | 72 | 72 | 82 | 89 |
| 5 | 47 | 56 | 69 | 73 | 69 | 73 | 5 | 87 | 88 | 71 | 68 | 69 | 86 |
| 10 | 58 | 62 | 78 | 81 | 77 | 78 | 10 | 92 | 84 | 82 | 86 | 78 | 80 |
| 20 | 74 | 79 | 80 | 83 | 78 | 88 | 20 | 88 | 89 | 87 | 90 | 92 | 82 |
| 30 | 83 | 85 | 83 | 89 | 90 | 94 | 30 | 100 | 96 | 94 | 96 | 100 | 96 |

TABLE 6

Herbicidal activity of composition 1.1 {compound(I) + compound(IID)}

| Wheat | | | | | | | Lambsquarters | | | | | | |
|---|---|---|---|---|---|---|---|---|---|---|---|---|---|
| IID\I | 0 | 1,5 | 5 | 10 | 20 | 30 | IID\I | 0 | 1,5 | 5 | 10 | 20 | 30 |
| 0 |  | +5 | +15 | +18 | +8 | +12 | 0 |  | 18 | 25 | 48 | 70 | 81 |
| 1,5 | 0 | +2 | +4 | +6 | +10 | +8 | 1,5 | 72 | 86 | 90 | 91 | 89 | 93 |
| 5 | 6 | 4 | 0 | +4 | +6 | +11 | 5 | 94 | 96 | 93 | 98 | 98 | 93 |
| 10 | 14 | 12 | 8 | 4 | +2 | 0 | 10 | 100 | 100 | 100 | 100 | 100 | 100 |
| 20 | 23 | 26 | 18 | 12 | 8 | 2 | 20 | 100 | 100 | 100 | 100 | 100 | 100 |
| 30 | 31 | 36 | 24 | 31 | 34 | 18 | 30 | 100 | 100 | 100 | 100 | 100 | 100 |
| Corn | | | | | | | Cotton | | | | | | |
| IID\I | 0 | 1,5 | 5 | 10 | 20 | 30 | IID\I | 0 | 1,5 | 5 | 10 | 20 | 30 |
| 0 |  | +4 | +8 | +15 | +12 | 2 | 0 |  | +8 | +12 | +23 | +11 | 8 |
| 1,5 | 38 | 12 | 0 | +4 | +11 | +10 | 1,5 | 23 | 8 | 4 | 0 | +4 | +2 |
| 5 | 54 | 36 | 24 | 12 | +14 | +8 | 5 | 41 | 36 | 16 | 11 | 2 | 6 |
| 10 | 72 | 56 | 48 | 14 | +2 | +6 | 10 | 64 | 58 | 55 | 14 | 6 | +1 |
| 20 | 82 | 79 | 81 | 76 | 16 | 2 | 20 | 72 | 78 | 68 | 74 | 24 | 14 |
| 30 | 86 | 88 | 93 | 88 | 93 | 28 | 30 | 86 | 82 | 92 | 83 | 78 | 68 |
| Soybean | | | | | | | Flax | | | | | | |
| IID\I | 0 | 1,5 | 5 | 10 | 20 | 30 | IID\I | 0 | 1,5 | 5 | 10 | 20 | 30 |
| 0 |  | +8 | +12 | +17 | +9 | +12 | 0 |  | 0 | +2 | +8 | +3 | 5 |
| 1,5 | 36 | 21 | 8 | +1 | +2 | +4 | 1,5 | 12 | 17 | 8 | 12 | 5 | 3 |

TABLE 6-continued

Herbicidal activity of composition 1.1 {compound(I) + compound(IID)}

| | | | Cocklebur | | | | | | | Wild mustard | | | |
|---|---|---|---|---|---|---|---|---|---|---|---|---|---|
| 5 | 52 | 33 | 18 | 21 | +6 | 2 | 5 | 19 | 14 | 13 | 4 | +3 | +8 |
| 10 | 67 | 66 | 55 | 48 | +8 | 4 | 10 | 26 | 23 | 18 | 16 | 13 | 6 |
| 20 | 83 | 88 | 78 | 61 | 60 | 31 | 20 | 33 | 42 | 37 | 28 | 27 | 10 |
| 30 | 96 | 100 | 91 | 100 | 83 | 92 | 30 | 30 | 41 | 24 | 33 | 32 | 18 |

| IID\I | 0 | 1,5 | 5 | 10 | 20 | 30 | IID\I | 0 | 1,5 | 5 | 10 | 20 | 30 |
|---|---|---|---|---|---|---|---|---|---|---|---|---|---|
| 0 | | 0 | 0 | +2 | 12 | 17 | 0 | | 13 | 31 | 43 | 58 | 65 |
| 1,5 | 44 | 56 | 52 | 64 | 66 | 58 | 1,5 | 67 | 83 | 81 | 88 | 82 | 94 |
| 5 | 56 | 69 | 66 | 71 | 69 | 74 | 5 | 85 | 88 | 92 | 84 | 88 | 96 |
| 10 | 74 | 77 | 83 | 74 | 83 | 88 | 10 | 100 | 96 | 98 | 100 | 94 | 100 |
| 20 | 88 | 94 | 96 | 87 | 93 | 92 | 20 | 100 | 100 | 100 | 100 | 100 | 100 |
| 30 | 96 | 100 | 100 | 100 | 100 | 98 | 30 | 100 | 100 | 100 | 100 | 100 | 100 |

I claim:

1. A herbicidal composition comprising: from 1.5 to 30 parts by weight of a compound of formula (I)

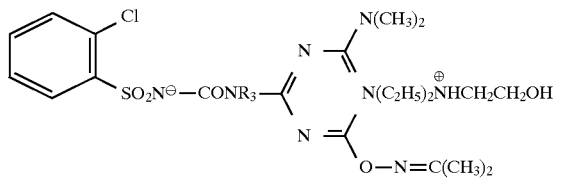

wherein $R_1$ is hydrogen or methyl;
from 1.5 to 30 parts by weight of a compound of formula (II)

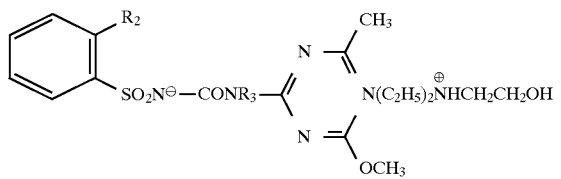

wherein $R_1$ is hydrogen or methyl and $R_2$ is chlorine, methoxycarbonyl or 2-chloroethoxy;
from 1.0 to 5.0 parts by weight of a surfactant selected from the group consisting of:
  bis-polyoxyethylated alkylamines, sodium bis(2-ethylhexyl)succinate sulfonate,
  polyethyleneglycol monoalkyl ethers, and
  alkylaryl ethers of polyethyleneglycol or polypropyleneglycol;
from 20 to 40 parts by weight of triethyleneglycol; and sufficient water to bring the total weight to 100 parts.

2. The composition of claim 1 wherein $R_1$ in formula (I) is hydrogen.

3. The composition of claim 1 wherein $R_1$ in formula (II) is hydrogen.

4. The composition of claim 2 wherein $R_1$ in formula (II) is hydrogen.

5. The composition of claim 1 wherein $R_2$ is chloro.

6. The composition of claim 1 wherein $R_2$ is methoxycarbonyl.

7. The composition of claim 1 wherein $R_2$ is chloroethoxy.

8. The composition of claim 2 wherein $R_2$ is chloro.

9. The composition of claim 2 wherein $R_2$ is methoxycarbonyl.

10. The composition of claim 2 wherein $R_2$ is chloroethoxy.

11. The composition of claim 3 wherein $R_2$ is chloro.

12. The composition of claim 3 wherein $R_2$ is methoxycarbonyl.

13. The composition of claim 3 wherein $R_2$ is chloroethoxy.

14. The composition of claim 4 wherein $R_2$ is chloro.

15. The composition of claim 4 wherein $R_2$ is methoxycarbonyl.

16. The composition of claim 4 wherein $R_2$ is chloroethoxy.

17. The composition of claim 2 wherein $R_1$ in formula (II) is methyl.

18. The composition of claim 17 wherein $R_2$ is methoxycarbonyl.

* * * * *

UNITED STATES PATENT AND TRADEMARK OFFICE
CERTIFICATE OF CORRECTION

PATENT NUMBER: 5,773,387
DATE OF ISSUE : June 30, 1998
INVENTOR : SOROKIN, Vladimir I.

It is certified that an error appears in the above-identified patent and that said Letters Patent is corrected as shown below:

In the first column of the cover page of the patent, delete the entity identified as the Assignee: "Labatt Brewing Company Limited. London, Canada"

and insert the correct Assignee -- R & D Kare International, Inc.
Van Nuys, California --

Signed and Sealed this

Twenty-third Day of March, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO.: 5,773,387
DATED : June 30, 1998
INVENTOR : SOROKIN, Vladimir I.

It is certified that errors appear in the above-identified patent and that said Letters Patent is hereby corrected as shown below:

Column 11, formula 2, "$R_3$" should be --$R_1$--.

Signed and Sealed this

Twenty-first Day of March, 2000

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO.: 5,773,387
DATED : June 30, 1998
INVENTOR : SOROKIN, Vladimir I.

It is certified that errors appear in the above-identified patent and that said Letters Patent is hereby corrected as shown below:

Column 11, formula 1, "$R_3$" should be --$R_1$--.

Signed and Sealed this

Twenty-second Day of August, 2000

Attest:

Q. TODD DICKINSON

*Attesting Officer*     *Director of Patents and Trademarks*